US009138249B2

United States Patent
Adams et al.

(10) Patent No.: US 9,138,249 B2
(45) Date of Patent: Sep. 22, 2015

(54) SHOCK WAVE CATHETER SYSTEM WITH ARC PRECONDITIONING

(71) Applicant: Shockwave Medical, Inc., Bellevue, WA (US)

(72) Inventors: John Adams, Snohomish, WA (US); Randy Holmberg, Bothell, WA (US)

(73) Assignee: SHOCKWAVE MEDICAL, INC., Fremont, CA (US)

( * ) Notice: Subject to any disclaimer, the term of this patent is extended or adjusted under 35 U.S.C. 154(b) by 388 days.

(21) Appl. No.: 13/777,807

(22) Filed: Feb. 26, 2013

(65) Prior Publication Data

US 2014/0052145 A1    Feb. 20, 2014

Related U.S. Application Data

(60) Provisional application No. 61/684,398, filed on Aug. 17, 2012.

(51) Int. Cl.
| | |
|---|---|
| *A61B 17/22* | (2006.01) |
| *A61B 17/225* | (2006.01) |
| *F17D 3/00* | (2006.01) |
| *A61B 17/00* | (2006.01) |

(52) U.S. Cl.
CPC ........... *A61B 17/225* (2013.01); *A61B 17/2202* (2013.01); *A61B 17/22022* (2013.01); *F17D 3/00* (2013.01); *A61B 2017/00159* (2013.01); *A61B 2017/00176* (2013.01); *A61B 2017/22021* (2013.01); *A61B 2017/22062* (2013.01); *Y10T 137/0391* (2015.04)

(58) Field of Classification Search
CPC ........... A61B 17/225; A61B 17/22022; A61B 17/2202; A61B 2017/22021; A61B 2017/00176; A61B 2017/22062; A61B 2017/22064

See application file for complete search history.

(56) References Cited

U.S. PATENT DOCUMENTS

| | | |
|---|---|---|
| 3,785,382 A | 1/1974 | Schmidt et al. |
| 3,902,499 A | 9/1975 | Shene |
| 4,027,674 A | 6/1977 | Tessler et al. |
| 4,662,126 A | 5/1987 | Malcolm |

(Continued)

FOREIGN PATENT DOCUMENTS

| | | |
|---|---|---|
| DE | 3038445 A1 | 5/1982 |
| EP | 0442199 A2 | 8/1991 |

(Continued)

OTHER PUBLICATIONS

Advisory Action Received for U.S. Appl. No. 12/581,295, mailed on Jul. 3, 2014, 3 pages.

(Continued)

*Primary Examiner* — Jonathan W Miles

(74) *Attorney, Agent, or Firm* — Morrison & Foerster LLP

(57) ABSTRACT

A shock wave catheter system and method produces a shock wave with reduced energy. The system includes a catheter and a power source. The catheter has an elongated carrier and a balloon about the carrier in sealed relation thereto. The balloon is arranged to receive a fluid therein that inflates the balloon. The catheter further includes an arc generator including at least two electrodes within the balloon. The power source is coupled to the at least two electrodes and is configured to grow a bubble at one of the at least two electrodes and then thereafter to rapidly expand the bubble to form a shock wave within the balloon.

9 Claims, 3 Drawing Sheets

(56) References Cited

U.S. PATENT DOCUMENTS

| | | | |
|---|---|---|---|
| 4,685,458 A | 8/1987 | Leckrone | |
| 4,809,682 A | 3/1989 | Forssmann et al. | |
| 4,900,303 A | 2/1990 | Lemelson | |
| 5,009,232 A | 4/1991 | Hassler et al. | |
| 5,057,103 A | 10/1991 | Davis | |
| 5,078,717 A | 1/1992 | Parins et al. | |
| 5,103,804 A | 4/1992 | Abele et al. | |
| 5,152,767 A | 10/1992 | Sypal et al. | |
| 5,152,768 A | 10/1992 | Bhatta | |
| 5,176,675 A | 1/1993 | Watson et al. | |
| 5,245,988 A | 9/1993 | Einars et al. | |
| 5,246,447 A | 9/1993 | Rosen et al. | |
| 5,281,231 A | 1/1994 | Rosen et al. | |
| 5,321,715 A * | 6/1994 | Trost | 372/69 |
| 5,324,255 A | 6/1994 | Passafaro et al. | |
| 5,336,234 A | 8/1994 | Vigil et al. | |
| 5,362,309 A * | 11/1994 | Carter | 604/22 |
| 5,368,591 A | 11/1994 | Lennox et al. | |
| 5,395,335 A | 3/1995 | Jang | |
| 5,417,208 A | 5/1995 | Winkler | |
| 5,425,735 A | 6/1995 | Rosen et al. | |
| 5,472,406 A | 12/1995 | de la Torre et al. | |
| 5,582,578 A | 12/1996 | Zhong et al. | |
| 5,603,731 A | 2/1997 | Whitney | |
| 5,609,606 A | 3/1997 | O'Boyle | |
| 5,662,590 A | 9/1997 | de la Torre et al. | |
| 5,931,805 A | 8/1999 | Brisken | |
| 6,007,530 A | 12/1999 | Dornhofer et al. | |
| 6,033,371 A | 3/2000 | Torre et al. | |
| 6,083,232 A | 7/2000 | Cox | |
| 6,210,408 B1 | 4/2001 | Chandrasekaran et al. | |
| 6,217,531 B1 | 4/2001 | Reitmajer | |
| 6,277,138 B1 | 8/2001 | Levinson et al. | |
| 6,287,272 B1 | 9/2001 | Brisken et al. | |
| 6,352,535 B1 | 3/2002 | Lewis et al. | |
| 6,367,203 B1 | 4/2002 | Graham et al. | |
| 6,371,971 B1 | 4/2002 | Tsugita et al. | |
| 6,398,792 B1 | 6/2002 | O'Connor | |
| 6,406,486 B1 | 6/2002 | de la Torre et al. | |
| 6,514,203 B2 | 2/2003 | Bukshpan | |
| 6,524,251 B2 | 2/2003 | Rabiner et al. | |
| 6,589,253 B1 | 7/2003 | Cornish et al. | |
| 6,607,003 B1 | 8/2003 | Wilson | |
| 6,638,246 B1 | 10/2003 | Naimark et al. | |
| 6,652,547 B2 | 11/2003 | Rabiner et al. | |
| 6,736,784 B1 | 5/2004 | Menne et al. | |
| 6,740,081 B2 | 5/2004 | Hilal | |
| 6,755,821 B1 | 6/2004 | Fry | |
| 6,989,009 B2 | 1/2006 | Lafontaine | |
| 7,241,295 B2 | 7/2007 | Maguire | |
| 7,569,032 B2 | 8/2009 | Naimark et al. | |
| 8,556,813 B2 | 10/2013 | Cioanta et al. | |
| 8,728,091 B2 | 5/2014 | Hakala et al. | |
| 9,011,463 B2 * | 4/2015 | Adams et al. | 606/128 |
| 2001/0044596 A1 | 11/2001 | Jaafar | |
| 2002/0045890 A1 * | 4/2002 | Celliers et al. | 606/7 |
| 2002/0177889 A1 | 11/2002 | Brisken et al. | |
| 2003/0004434 A1 | 1/2003 | Greco et al. | |
| 2003/0176873 A1 | 9/2003 | Chernenko et al. | |
| 2003/0229370 A1 | 12/2003 | Miller | |
| 2004/0044308 A1 | 3/2004 | Naimark et al. | |
| 2004/0097963 A1 * | 5/2004 | Seddon | 606/127 |
| 2004/0097996 A1 | 5/2004 | Rabiner et al. | |
| 2004/0162508 A1 * | 8/2004 | Uebelacker | 601/2 |
| 2004/0254570 A1 | 12/2004 | Hadjicostis et al. | |
| 2005/0015953 A1 | 1/2005 | Keidar | |
| 2005/0021013 A1 | 1/2005 | Visuri et al. | |
| 2005/0251131 A1 | 11/2005 | Lesh | |
| 2006/0004286 A1 | 1/2006 | Chang et al. | |
| 2006/0184076 A1 | 8/2006 | Gill et al. | |
| 2006/0190022 A1 | 8/2006 | Beyar et al. | |
| 2007/0088380 A1 | 4/2007 | Hirszowicz et al. | |
| 2007/0239082 A1 | 10/2007 | Schultheiss et al. | |
| 2007/0239253 A1 | 10/2007 | Jagger et al. | |
| 2007/0244423 A1 | 10/2007 | Zumeris et al. | |
| 2008/0097251 A1 | 4/2008 | Babaev | |
| 2008/0188913 A1 | 8/2008 | Stone et al. | |
| 2009/0041833 A1 | 2/2009 | Bettinger et al. | |
| 2009/0247945 A1 | 10/2009 | Levit et al. | |
| 2009/0254114 A1 | 10/2009 | Hirszowicz et al. | |
| 2009/0312768 A1 | 12/2009 | Hawkins et al. | |
| 2010/0016862 A1 | 1/2010 | Hawkins et al. | |
| 2010/0036294 A1 | 2/2010 | Mantell et al. | |
| 2010/0114020 A1 | 5/2010 | Hawkins et al. | |
| 2010/0114065 A1 | 5/2010 | Hawkins et al. | |
| 2010/0121322 A1 | 5/2010 | Swanson | |
| 2010/0305565 A1 | 12/2010 | Truckai et al. | |
| 2011/0034832 A1 | 2/2011 | Cioanta et al. | |
| 2011/0118634 A1 | 5/2011 | Golan | |
| 2011/0166570 A1 | 7/2011 | Hawkins et al. | |
| 2011/0257523 A1 | 10/2011 | Hastings et al. | |
| 2011/0295227 A1 | 12/2011 | Hawkins et al. | |
| 2012/0071889 A1 | 3/2012 | Mantell et al. | |
| 2012/0095461 A1 | 4/2012 | Herscher et al. | |
| 2012/0203255 A1 | 8/2012 | Hawkins et al. | |
| 2012/0221013 A1 | 8/2012 | Hawkins et al. | |
| 2013/0030431 A1 | 1/2013 | Adams | |
| 2013/0030447 A1 | 1/2013 | Adams | |
| 2013/0150874 A1 | 6/2013 | Kassab | |
| 2014/0046229 A1 | 2/2014 | Hawkins et al. | |
| 2014/0052147 A1 | 2/2014 | Hakala et al. | |
| 2014/0074111 A1 | 3/2014 | Hakala et al. | |
| 2014/0243820 A1 | 8/2014 | Adams et al. | |
| 2014/0243847 A1 | 8/2014 | Hakala et al. | |

FOREIGN PATENT DOCUMENTS

| | | |
|---|---|---|
| EP | 0571306 A1 | 11/1993 |
| JP | 62-275446 A | 11/1987 |
| JP | 6-125915 A | 5/1994 |
| JP | 7-47135 A | 2/1995 |
| JP | 10-99444 A | 4/1998 |
| JP | 10-513379 A | 12/1998 |
| JP | 2002-538932 A | 11/2002 |
| JP | 2004-81374 A | 3/2004 |
| JP | 2005-95410 A | 4/2005 |
| JP | 2005-515825 A | 6/2005 |
| JP | 2006-516465 A | 7/2006 |
| WO | 96/24297 A1 | 8/1996 |
| WO | 2004/069072 A2 | 8/2004 |
| WO | 2006/127158 A2 | 11/2006 |
| WO | 2007/149905 A2 | 12/2007 |
| WO | 2009/121017 A1 | 10/2009 |
| WO | 2009/152352 A2 | 12/2009 |
| WO | 2010/014515 A2 | 2/2010 |
| WO | 2011/143468 A2 | 11/2011 |
| WO | 2013/059735 A1 | 4/2013 |

OTHER PUBLICATIONS

Notice of Allowance received for U.S. Appl. No. 13/831,543, mailed on Oct. 8, 2014, 14 pages.

Non-Final Office Action received for U.S. Appl. No. 14/271,342, mailed on Sep. 2, 2014, 6 pages.

Notice of Acceptance Received for Australian Patent Application No. 2009257368, mailed on Aug. 28, 2014, 2 pages.

Doug Hakala, "Unpublished U.S. Appl. No. 14/515,130, filed Oct. 15, 2014, titled "Low Profile Electrodes for an Angioplasty Shock Wave Catheter"".

Non Final Office Action received for U.S. Appl. No. 13/465,264, mailed on Oct. 29, 2014, 13 pages.

Non Final Office Action received for U.S. Appl. No. 13/646,570, mailed on Oct. 29, 2014, 10 pages.

Non-Final Office Action received for U.S. Appl. No. 13/646,583, mailed on Oct. 31, 2014, 8 pages.

Written Opinon received for PCT Patent Application No. PCT/US2009/047070, mailed on Jan. 19, 2010, 5 pages.

International Preliminary Report on Patentability received for PCT Patent Application No. PCT/US2009/047070, mailed on Dec. 23, 2010, 7 pages.

International Search Report received for PCT Patent Application No. PCT/US2009/047070, mailed on Jan. 19, 2010, 4 pages.

(56) References Cited

OTHER PUBLICATIONS

International Preliminary Report on Patentability received for PCT Patent Application No. PCT/US2011/047070, mailed on Feb. 21, 2013, 7 pages.
International Written Opinion received for PCT Patent Application No. PCT/US2011/047070, mailed on May 1, 2012, 5 pages.
International Search Report received for PCT Patent Application No. PCT/US2012/023172, mailed on Sep. 28, 2012, 3 pages.
International Search Report and Written Opinion received for PCT Patent Application No. PCT/US2013/031805 mailed on May 20, 2013, 13 pages.
Adams et al., U.S. Appl. No. 13/534,658, filed Jun. 27, 2012, titled "Shock Wave Balloon Catheter with Multiple Shock Wave Sources".
Hakala et al., U.S. Appl. No. 13/615,107, filed Sep. 13, 2012, titled "Shockwave Catheter System with Energy Control".
Non Final Office Action received for U.S. Appl. No. 12/482,995, mailed on Jul. 12, 2013, 11 pages.
Hakala et al., U.S. Appl. No. 13/831,543, filed Mar. 14, 2013, titled "Low Profile Electrodes for an Angioplasty Shock Wave Catheter", 52 pages.
International Preliminary Report on Patentability received for PCT Patent Application No. PCT/US2012/023172, mailed on Aug. 15, 2013, 6 pages.
International Search Report and Written Opinion received for PCT Patent Application No. PCT/US2013/039987, mailed on Sep. 23, 2013, 15 pages.
International Search Report and Written Opinion received for PCT Patent Application No. PCT/US2013/048277, mailed on Oct. 2, 2013, 14 pages.
Office Action received for Australian Patent Application No. 2009257368, issued on Jul. 31, 2013, 4 pages.
Office Action received for Japanese Patent Application No. 2011-513694, mailed on Aug. 27, 2013, 6 pages (3 pages of English Translation).
Rosenschein et al., "Shock-Wave Thrombus Ablation, a New Method for Noninvasive Mechanical Thrombolysis", The American Journal of Cardiology, vol. 70, Nov. 15, 1992, pp. 1358-1361.
Zhong et al., "Transient Oscillation of Cavitation Bubbles Near Stone Surface During Electohydraulic Lithotripsy", Journal of Endourology, vol. 11, No. 1, Feb. 1997, pp. 55-61.
Extended European Search Report (includes Supplementary European Search Report and Search Opinion) received for European Patent Application No. 097636401, mailed on Oct. 10, 2013, 5 pages.
Final Office Action received for U.S. Appl. No. 13/267,383, mailed on Oct. 25, 2013, 8 pages.
International Search Report and Written Opinion received for PCT Patent Application No. PCT/US2013/059533, mailed on Nov. 7, 2013, 14 pages.
Hakala et al., "Unpublished U.S. Appl. No. 14/271,276, filed May 6, 2014, titled "Shockwave Catheter System with Energy Control"", 20 pages.
International Search Report and Written Opinion received for PCT Patent Application No. PCT/US2013/055431, mailed on Nov. 12, 2013, 9 pages.
Advisory Action received for U.S. Appl. No. 13/267,383, mailed on Jan. 6, 2014, 4 pages.
Non-Final Office Action received for U.S. Appl. No. 12/501,619, mailed on Jan. 28, 2014, 10 pages.
Non-Final Office Action received for U.S. Appl. No. 13/049,199, mailed on Feb. 4, 2014, 8 pages.
Final Office Action received for U.S. Appl. No. 12/482,995, mailed on Feb. 20, 2014, 11 pages.
Non Final Office Action received for U.S. Appl. No. 12/482,995, mailed on Aug. 13, 2014, 10 pages.
Final Office Action received for U.S. Appl. No. 12/581,295, mailed on Jun. 5, 2014, 14 pages.
Non-Final Office Action received for U.S. Appl. No. 12/581,295, mailed on Mar. 10, 2014, 11 pages.
Final Office Action received for U.S. Appl. No. 13/049,199, mailed on Aug. 11, 2014, 8 pages.
Non-Final Office Action received for U.S. Appl. No. 14/061,554, mailed on Mar. 12, 2014, 14 pages.
Notice of Allowance received for U.S. Appl. No. 14/061,554, mailed on Apr. 25, 2014, 8 pages.
Non Final Office Action received for U.S. Appl. No. 14/079,463, mailed on Mar. 4, 2014, 9 pages.
Notice of Allowance received for U.S. Appl. No. 14/079,463, mailed on Apr. 1, 2014, 5 pages.
Non-Final Office Action received for U.S. Appl. No. 14/271,276, mailed on Aug. 4, 2014, 7 pages.
Office Action received for Australian Patent Application No. 2009257368, issued on Apr. 28, 2014, 4 pages.
Office Action Received for Japanese Patent Application No. 2011-513694, mailed on Jun. 10, 2014, (See Communication under 37 CFR § 1.98(a) (3)).
Adams et al., "Unpublished U.S. Appl. No. 14/271,342, filed May 6, 2014, titled "Shock Wave Balloon Catheter with Multiple Shock Wave Sources"", 21 pages.
Adams, John M., "Unpublished U.S. Appl. No. 14/218,858, filed Mar. 18, 2014, titled "Shockwave Catheter System with Energy Control"", 24 pages.
Cleveland et al., "The Physics of Shock Wave Lithotripsy", Extracorporeal Shock Wave Lithotripsy Part IV, Chapter 38, 2012, pp. 316-332.
Connors et al., "Renal Nerves Mediate Changes in Contralateral Renal Blood Flow after Extracorporeal Shockwave Lithotripsy", Nephron Physiol., vol. 95, 2003, pp. 67-75.
Gambihler et al., "Permeabilization of the Plasma Membrane of L1210 Mouse Leukemia Cells Using Lithotripter Shock Waves", The Journal of Membrane Biology, vol. 141, 1994, pp. 267-275.
Grassi et al., "Novel Antihypertensive Therapies: Renal Sympathetic Nerve Ablation and Carotid Baroreceptor Stimulation", Curr. Hypertens Rep., vol. 14, 2012, pp. 567-572.
Kodama et al., "Shock Wave-Mediated Molecular Delivery Into Cells", Biochimica et Biophysica Acta, vol. 1542, 2002, pp. 186-194.
Lauer et al., "Shock Wave Permeabilization as a New Gene Transfer Method", Gene Therapy vol. 4, 1997, pp. 710-715.

\* cited by examiner

SHOCK WAVE CATHETER SYSTEM WITH ARC PRECONDITIONING

PRIORITY CLAIM

The present application claims the benefit of copending U.S. Provisional Patent Application Ser. No. 61/684,398, filed Aug. 17, 2012, which application is incorporated herein by reference in its entirety.

BACKGROUND OF THE INVENTION

The present invention relates to a treatment system for percutaneous coronary angioplasty or peripheral angioplasty in which a dilation catheter is used to cross a lesion in order to dilate the lesion and restore normal blood flow in the artery. It is particularly useful when the lesion is a calcified lesion in the wall of the artery.

Calcified lesions, currently treated with angioplasty balloons, require high pressures (sometimes as high as 10-15 or even 30 atmospheres) to break the calcified plaque and push it back into the vessel wall. With such pressures comes trauma to the vessel wall which can contribute to vessel rebound, dissection, thrombus formation, and a high level of restenosis. Non-concentric calcified lesions can result in undue stress to the free wall of the vessel when exposed to high pressures. An angioplasty balloon when inflated to high pressures can have a specific maximum diameter to which it will expand but the opening in the vessel under a concentric lesion will typically be much smaller. As the pressure is increased to open the passage way for blood the balloon will be confined to the size of the opening in the calcified lesion (before it is broken open). As the pressure builds a tremendous amount of energy is stored in the balloon until the calcified lesion breaks or cracks. That energy is then released and results in the rapid expansion of the balloon to its maximum dimension and may stress and injure the vessel walls.

Recently, a new system and method has been contemplated for breaking up calcium deposits in, for example, arteries and veins. Such a system is described, for example in U.S. Patent Publication No. 2009/0312768, Published Dec. 17, 2009. Embodiments described therein include a catheter having balloon, such as an angioplasty balloon, at the distal end thereof, arranged to be inflated with a fluid. Disposed within the balloon is a shock wave generator that may take the form of, for example, a pair of electrodes, which are coupled to a high voltage source at the proximal end of the catheter through a connector. When the balloon is placed adjacent a calcified region of a vein or artery and a high voltage pulse is applied across the electrodes, a shock wave is formed that propagates through the fluid and impinges upon the wall of the balloon and the calcified region. Repeated pulses break up the calcium without damaging surrounding soft tissue.

Each high voltage pulse causes an arc to form across the electrodes. The arc in turn causes a steam bubble to form. Each arc results in intense heat and energy for a brief period of time. Inside the small confines of tiny angioplasty balloons the fluid can warm up and become hot enough to damage tissue unless steps are taken to control the amount of energy released into the fluid. Just a two degree Celsius elevation in temperature above body temperature can result in tissue damage.

The amount of energy to assure the formation of the steam bubble and arc can be highly variable from arc to arc. Therefore, if the same amount of energy is used to assure the formation of each bubble and arc, more energy than is necessary will be used to form many of the bubbles and arcs. Excessive heating of the fluid within the balloon may result. Also, because greater applied energies create larger bubbles at the electrodes, the excessive energy will produce a larger bubble than required which can unduly stress the balloon walls.

Another consideration is the amount of energy represented by the high voltage applied to the electrodes. Each high voltage pulse removes a portion of the electrode material. Since the size of the electrodes must be small in order to fit into the calcified vein or artery, they are only capable of sustaining a limited numbers of high voltage pulses sufficient to form the shock wave resulting electrical arc.

Hence, there is a need in the art to be able to control the amount of energy required to produce the bubbles and arcs. It would also be desirable to be able to produce the bubbles and arcs with less energy than hereto for possible. The present invention addresses these and other issues.

SUMMARY OF THE INVENTION

In one embodiment, a shock wave catheter system includes a catheter and a power source. The catheter has an elongated carrier and a balloon about the carrier in sealed relation thereto. The balloon is arranged to receive a fluid therein that inflates the balloon. The catheter further includes an arc generator including at least two electrodes within the balloon. The power source is configured to deliver a first electrical voltage across the at least two electrodes that grows a bubble at one of the at least two electrodes and then thereafter delivers a second electrical voltage across the at least two electrodes to create an arc across the at least two electrodes to rapidly expand the bubble to form a shock wave within the balloon.

The second electrical voltage is significantly greater than the first electrical voltage. The first electrical voltage is on the order of 50 volts and the second electrical voltage is between 300 and 10,000 volts.

The power source may be configured to hold the first electrical voltage for a first time period and to hold the second electrical voltage for a second time period, the first time period being significantly longer in length than the second time period. The first time period may on the order of two milliseconds and the second time period may be on the order of one-half microsecond.

The balloon may be an angioplasty balloon.

According to other embodiments, a shock wave catheter system includes a catheter and a power source. The catheter has an elongated carrier and a balloon about the carrier in sealed relation thereto. The balloon is arranged to receive a fluid therein that inflates the balloon. The catheter further has an arc generator including at least two electrodes within the balloon. The power source is coupled to the at least two electrodes and is configured to grow a bubble at one of the at least two electrodes and then thereafter to rapidly expand the bubble to form a shock wave within the balloon.

In another embodiment, a method of producing an electrohydraulic shock wave includes growing a bubble within a fluid during a first time period and thereafter, rapidly expanding the bubble during a second time period.

The growing step may include providing at least two electrodes within the fluid and delivering a first voltage to the at least two electrodes during a first time period.

The expanding step may include delivering a second voltage to the at least two electrodes during a second time period. The second voltage may be greater than the first voltage and the first time period may be longer than the second time period. The second voltage may be between 300 and 10,000 volts. The first time period may be on the order of two milliseconds and the second time period may be on the order of one-half microsecond.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

DETAILED DESCRIPTION OF THE INVENTION

Figure 1:
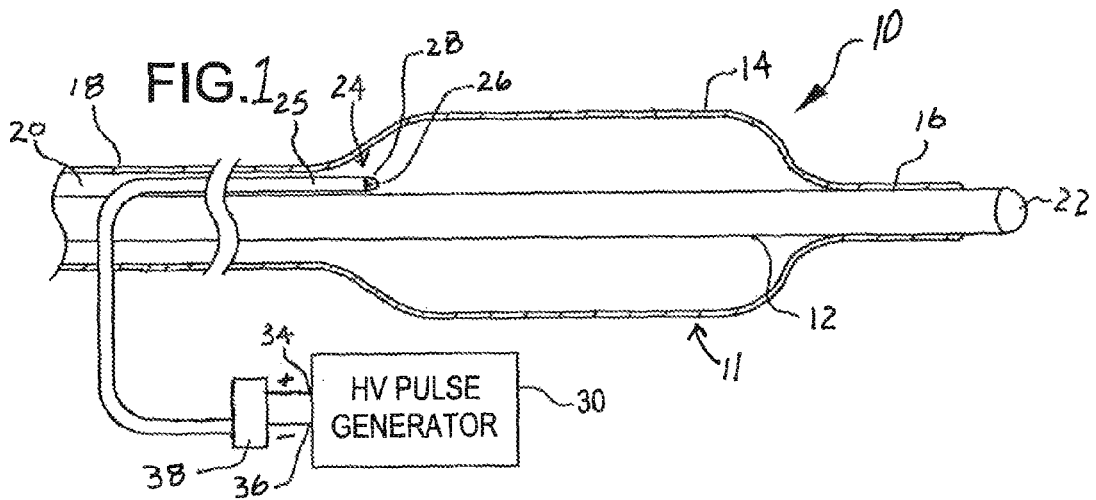
FIG. 1 is a simplified side view of an a shock wave catheter system embodying various embodiments of the invention to advantage.

FIG. 1 is a simplified side view of an angioplasty balloon catheter system 10 of the type that may utilize various embodiments of the invention to advantage. The system 10 includes a catheter 11 and a power source 30.

The catheter 11 includes an elongated carrier, such as a hollow sheath 12 and a dilating balloon 14 formed about the sheath 12 in sealed relation thereto at a seal 16. The balloon 14 has a tubular extension 18 which forms with the sheath 12 a channel 20 for admitting a fluid into the balloon 14. The sheath 12 has a longitudinal lumen 22 through which a guide wire (not shown) may be received for directing the catheter 11 to a desired location within a vein or artery, for example.

The catheter 11 further includes an arc generator 24 within the balloon 14. The arc generator, as may be best seen in FIG. 2, includes a lead 25 having a coaxially configured electrode pair including electrodes 26 and 28. As may be seen in FIG. 2, electrode 26 forms a center electrode and electrode 28 forms a ring shaped electrode concentrically disposed about the center electrode 26. As mentioned above, the sheath 12 forms with the balloon extension 18 a channel 20 through which fluid, such as saline, may be admitted into the balloon to inflate the balloon. The channel 20 further permits the electrodes 26 and 28 of lead 25 to be fed into the balloon 14.

Figure 2:
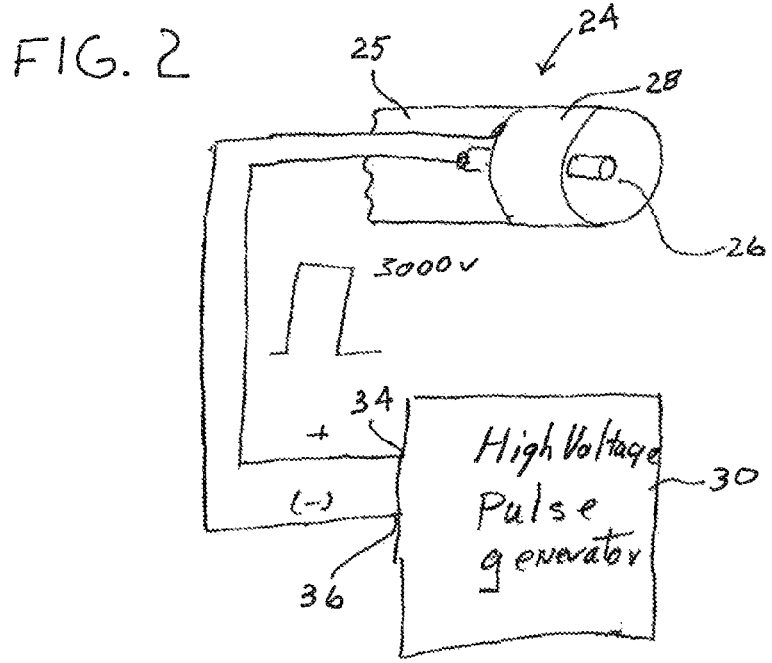
FIG. 2 is a simplified view, partly in perspective, of the electrode structure and power source employed in the catheter of FIG. 1.

As may be seen in FIGS. 1 and 2, the electrodes 26 and 28 are attached to a source 30 of high voltage pulses. As may be seen in FIG. 2, the center electrode 26 is coupled to a positive terminal 34 of source 30 and the ring electrode 28 is coupled to a negative terminal 36 of the source 30. The electrodes 26 and 28 may be formed of metal, such as stainless steel, and are maintained a controlled distance apart to allow a reproducible arc to form for a given applied voltage and current.

The electrical arcs between electrodes 26 and 28 in the fluid are used to generate shock waves in the fluid. Each pulse of high voltage applied to the electrodes 26 and 28 forms an arc across the electrodes. The voltage pulses may have amplitudes as low as 500 volts, but preferably, the voltage amplitudes are in the range of 1000 volts to 10,000 volts The balloon 14 may be filled with water or saline in order to gently fix the balloon in the walls of the artery or vein, for example, in direct proximity with the calcified lesion. The fluid may also contain an x-ray contrast to permit fluoroscopic viewing of the catheter during use. Once the catheter 11 is positioned with the guide wire (not shown), the physician or operator can start applying the high voltage pulses to the electrodes to form a plurality of discrete shock waves that crack the calcified plaque. Such shock waves will be conducted through the fluid, through the balloon, through the blood and vessel wall to the calcified lesion where the energy will break the hardened plaque without the application of excessive pressure by the balloon on the walls of the artery.

Figure 3:
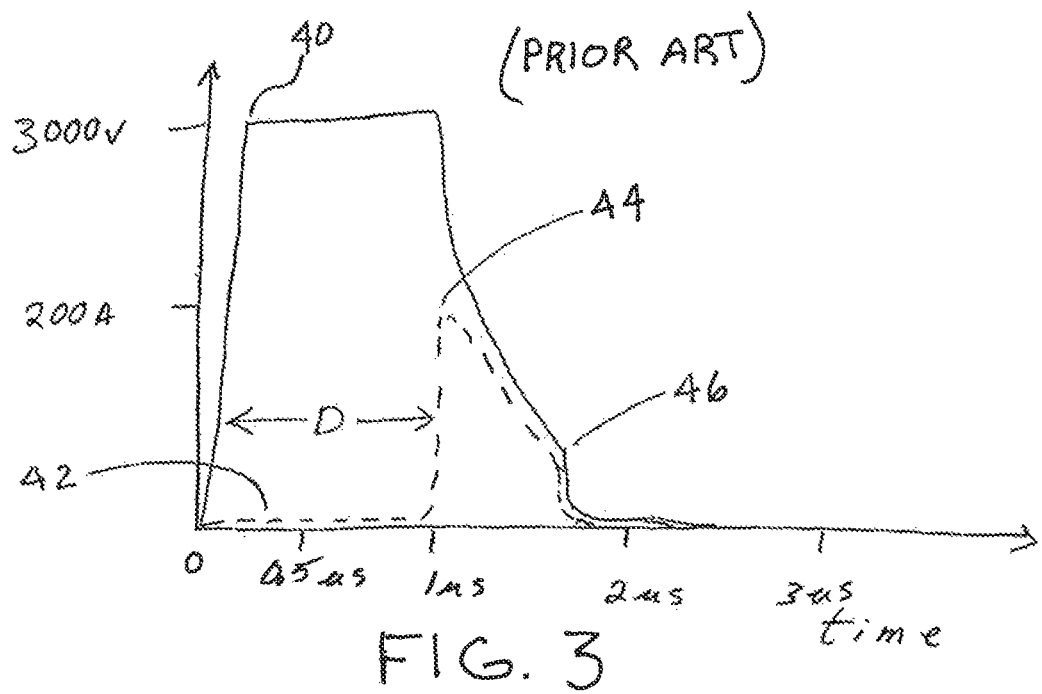
FIG. 3 is a graph illustrating typical voltage and current waveforms of voltage and current to form an electrohydraulic shock wave between a pair of electrodes as practiced in the prior art.

FIG. 3 is a graph illustrating typical voltage (solid line) and current (dashed line) waveforms of voltage and current if traditional prior art techniques are employed to form an electrohydraulic shock wave between a pair of electrodes, such as electrodes 26 and 28. Here it may be seen by reference character 40 that a voltage of 3,000 volts is applied between the electrodes. A low level current 42 flows through the water creating a bubble on the electrodes. After a delay D, for example one microsecond, at 44, an arc jumps across the bubble. In this example, the arc is 200 amperes and jumps between the electrodes. When the arc starts, the voltage drops quickly and when the voltage pulse is terminated at 46, it drops to zero. In this prior art methodology, the delay D is highly variable and has been measured to be as short as ninety nanoseconds to as long as 1000 nanoseconds. The delay D is also unpredictable from pulse to pulse. The shock wave is generated when the arc current occurs at 44. Since the delay D is unpredictable, the voltage pulse must be have a duration long enough to assure an arc will form. In the example, that duration is about 1.8 microseconds. The net result of a fixed long voltage is that more energy is applied to each pulse than is needed to assure the occurrence of an arc. The excess energy needlessly heats the fluid in the balloon.

Figure 4:
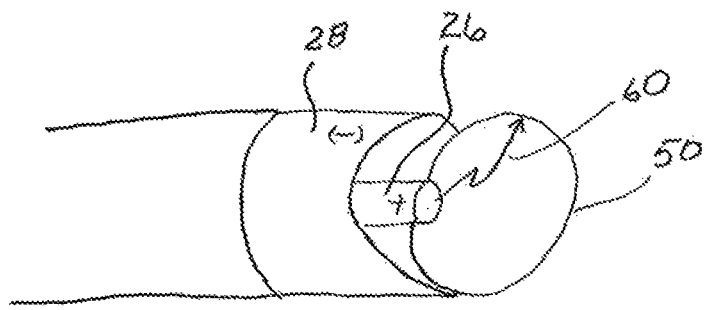
FIG. 4 is a simplified view, to an enlarged scale, illustrating the growth of a large bubble at an electrode.
Figure 5:
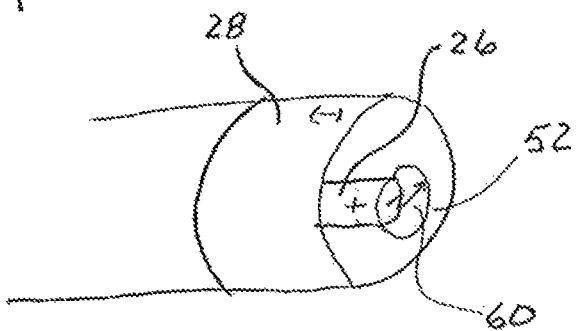
FIG. 5 is a simplified view, to an enlarged scale, illustrating the growth of a small bubble at an electrode.

FIGS. 4 and 5 illustrate the cause of the variable delay D. Sometimes, as shown in FIG. 4, a large bubble 50 is formed before the arc 60 occurs. However, at other times, a small bubble 52 is formed before the arc 60 occurs causing the arc to occur more quickly. The bubbles are formed by electrolysis of the fluid and a large bubble takes longer to form than a small bubble. The arc occurs when the voltage across the bubble is sufficient to arc the gap and is highly variable.

Figure 6:
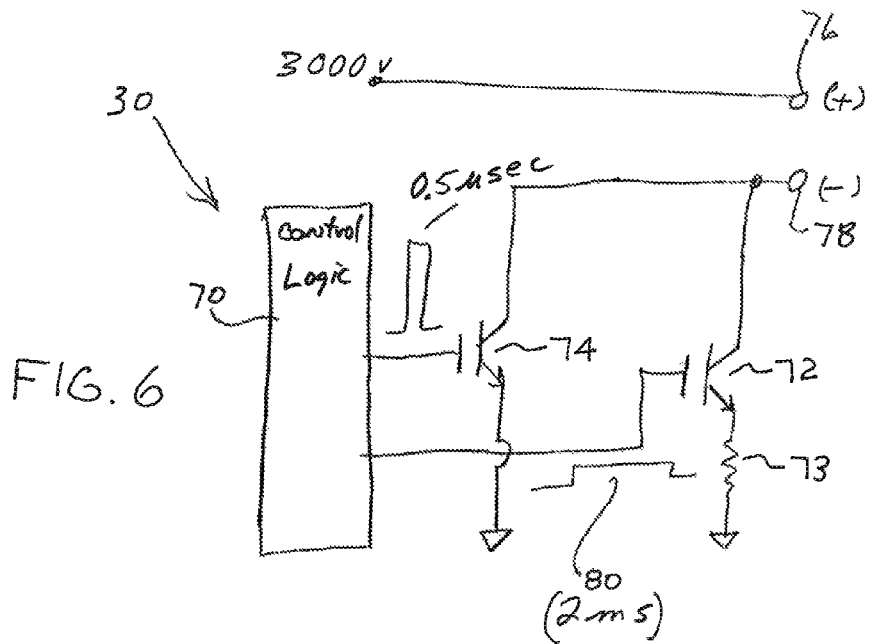
FIG. 6 is a schematic diagram of a power source for use in an angioplasty electrical arc shock wave angioplasty catheter system according to an embodiment of the invention.

FIG. 6 is a schematic diagram of a power source 30 for use in an angioplasty electrical arc shock wave angioplasty catheter system according to an embodiment of the invention. As will be seen, the power source delivers a first low voltage across the electrodes to pre-grow the bubble at one of the electrodes and thereafter delivers a second higher voltage across the electrodes to rapidly expand the pre-grown bubble to cause the arc and the shock wave in a time controlled manner.

The source 30 includes control logic 70, a first transistor 72, a second transistor 74, and output terminals 76 and 78. Output terminal 76 is arranged to coupled through a connector 38 (FIG. 1) to the center electrode 26 (FIG. 2) of the shock wave generator 24 and output 78 is arranged to be coupled through the connector to the outer electrode 28 of the shock wave generator. The output terminal is connected to a 3,000 volts source.

Initially, the control logic 70 delivers a two millisecond (2 ms) control pulse 80 to the gate of transistor 72. This causes a low (for example, 25 ma) current through the electrodes and a resistor 73. The low current applied for 2 ms forms a bubble on one of the electrodes of a predictable size. After the 2 ms, the control logic 70 turns transistor 74 on hard for 500 nanoseconds (500 ns). This applies the full 3,000 volts to the electrodes. The control logic 70 may turn transistor 74 on hard immediately after the 2 ms period or a short time thereafter, as for example, 10 microseconds after the 2 ms period. An arc and shock wave will occur essentially immediately. Since the high voltage is applied for only a short time, here 500 ns, a reduced amount of energy is delivered to the fluid within the balloon for generating each shock wave. As a result, much less heat is generated in the fluid within the balloon.

Figure 7:
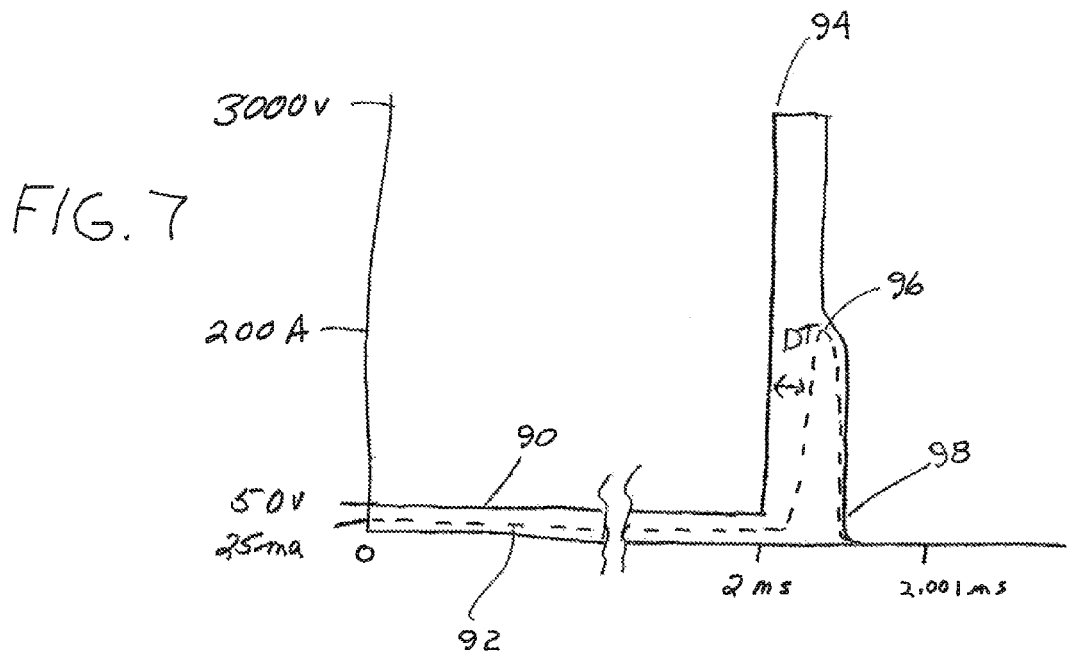
FIG. 7 is a graph illustrating voltage and current waveforms of voltage and current which may be derived from the power circuit of FIG. 6 to form an electrohydraulic shock wave between a pair of electrodes as practiced according to an embodiment of the invention.

FIG. 7 is a graph illustrating voltage and current waveforms of voltage (solid line) and current (dashed line) which may be derived from the power source 30 of FIG. 6 to form an electrohydraulic shock wave between the pair of electrodes 26 and 28 as practiced according to the embodiment of FIG. 6. First, a low voltage 90 is applied across the electrodes when transistor 72 is turned on for 2 ms. The low voltage assures that an arc will not occur across the electrodes. However, the low voltage does produce a low current 92 (25 ma) to flow through the electrodes. During this 2 ms period, a bubble of predictable size is grown on one of the electrodes. The bubble size may be controlled by the amount of current and the length of time the low current is applied. After the 2 ms period, the transistor 74 is turned on hard to apply a narrow pulse (500 ns) of the full 3,000 volt high voltage 94 across the electrodes. During this short time, a current of 250 amperes may flow between the electrodes. The high voltage and current rapidly expands the pre-grown bubble and within a short delay time DT causes the arc and shock wave to be produced at 96. The arc and shock wave are produced quickly because the bubble had already been pre-grown by the low voltage 90. The voltage and current fall quickly to zero at 98.

As may be seen from the foregoing, the high voltage pulse is applied for a much shorter period of time to produce the arc and shock wave because the bubble had already been pre-grown by the preceding low voltage and current. The overall arc energy is lower and the steam bubble will be smaller. This results in less energy being applied to the fluid within the balloon for each generated shock wave. The fluid is therefore heated less and there is less stress on the wall of the balloon.

While particular embodiments of the present invention have been shown and described, modifications may be made. It is therefore intended in the appended claims to cover all such changes and modifications which fall within the true spirit and scope of the invention as defined by those claims.

What is claimed is:

1. A shock wave catheter system, comprising:
   a catheter having an elongated carrier, a balloon about the carrier in sealed relation thereto, the balloon being arranged to receive a fluid therein that inflates the balloon, and an arc generator including at least two electrodes within the balloon; and
   a power source that delivers a first electrical voltage across the at least two electrodes that grows a bubble at one of the at least two electrodes wherein the first voltage is insufficient to create an arc across the electrodes and then thereafter delivers a second electrical voltage across the at least two electrodes, with the second voltage being greater than the first voltage and sufficient to create an arc across the at least two electrodes and to rapidly expand the bubble to form a shock wave within the balloon.

2. The shock wave catheter system of claim 1, wherein the first electrical voltage is on the order of 50 volts and the second electrical voltage is between 300 and 10,000 volts.

3. The shock wave catheter system of claim 1, wherein the power source is configured to hold the first electrical voltage for a first time period and to hold the second electrical voltage for a second time period, the first time period being longer in length than the second time period.

4. The shock wave catheter system of claim 3, wherein the first time period is on the order of two milliseconds and the second time period is on the order of one-half microsecond.

5. The shock wave catheter system of claim 1, wherein the balloon is an angioplasty balloon.

6. A method of producing an electrohydraulic shock wave in a vessel to treat calcified lesions comprising the steps of:
   advancing a catheter into the vessel, said catheter having an elongated carrier and a balloon about the carrier in sealed relation thereto, and an arc generator including at least two electrodes within the balloon;
   inflating the balloon with fluid;
   applying a first voltage across the electrodes to grow a bubble within the fluid during a first time period wherein the first voltage is insufficient to create an arc across the electrodes; and thereafter,
   applying a second voltage across the electrodes to rapidly expand the bubble during a second time period with the second voltage being greater than the first voltage and sufficient to create an arc across the at least two electrodes, said rapidly expanding bubble forming a shock wave for treating the calcified lesion.

7. The method of claim 6 wherein the first time period is longer than the second time period.

8. The method of claim 6, wherein the second voltage is between 300 and 10,000 volts.

9. The method of claim 6 wherein the first time period is on the order of two milliseconds and the second time period is on the order of one-half microsecond.

* * * * *